US008431736B2

(12) United States Patent
Dhoot et al.

(10) Patent No.: US 8,431,736 B2
(45) Date of Patent: Apr. 30, 2013

(54) CRYSTALLINE FORMS OF THE DI-SODIUM SALT OF N-(5- CHLOROSALICYLOYL)-8-AMINOCAPRYLIC ACID

(75) Inventors: Nikhil Dhoot, Dombivli (IN); Steven Dinh, Briarcliff Manor, NY (US); Shingai Majuru, Brewster, NY (US); William Elliott Bay, Ridgefield, CT (US); JoAnne P. Corvino, Harrison, NY (US); Doris C. O'Toole, Carmel, NY (US)

(73) Assignee: Emisphere Technologies, Inc., Roseland, NJ (US)

(*) Notice: Subject to any disclaimer, the term of this patent is extended or adjusted under 35 U.S.C. 154(b) by 0 days.

(21) Appl. No.: 13/207,750

(22) Filed: Aug. 11, 2011

(65) Prior Publication Data
US 2012/0065128 A1    Mar. 15, 2012

Related U.S. Application Data

(62) Division of application No. 12/067,239, filed as application No. PCT/US2006/036455 on Sep. 18, 2006, now Pat. No. 8,026,392.

(60) Provisional application No. 60/718,829, filed on Sep. 19, 2005.

(51) Int. Cl.
*C07C 229/00*    (2006.01)

(52) U.S. Cl.
USPC .......................................................... 562/450

(58) Field of Classification Search ........................ None
See application file for complete search history.

(56) References Cited

U.S. PATENT DOCUMENTS

| 5,069,419 | A | 12/1991 | Jerman |
| 5,474,978 | A | 12/1995 | Bakaysa et al. |
| 5,773,647 | A | 6/1998 | Leone-Bay et al. |
| 6,126,140 | A | 10/2000 | Johnson et al. |
| 2002/0065255 | A1 | 5/2002 | Bay et al. |
| 2004/0087640 | A1 | 5/2004 | Ferro et al. |
| 2004/0106825 | A1 | 6/2004 | Bay et al. |
| 2005/0054557 | A1 | 3/2005 | Goldberg |
| 2006/0063821 | A1 | 3/2006 | Gopalsamy et al. |
| 2006/0078622 | A1 | 4/2006 | Majuru et al. |
| 2006/0078623 | A1 | 4/2006 | Dhoot et al. |
| 2006/0106110 | A1 | 5/2006 | Bateman et al. |

FOREIGN PATENT DOCUMENTS

| CA | 1234561 A1 | 3/1988 |
| EP | 1535625 A1 | 6/2005 |
| EP | 2006802407 A2 | 5/2008 |
| EP | 2006802406 A2 | 7/2008 |
| WO | 00/59863 | * 10/2000 |
| WO | WO-0059863 A1 | 10/2000 |
| WO | WO-0245754 A2 | 6/2002 |

(Continued)

OTHER PUBLICATIONS

Supplemental European Search Report mailed Aug. 4, 2010.

*Primary Examiner* — Karl J Puttlitz
(74) *Attorney, Agent, or Firm* — Blank Rome LLP

(57) ABSTRACT

The present invention relates to crystalline polymorphic forms of the di-sodium salt of N-(5-chlorosalicyloyl)-8-aminocaprylic acid, pharmaceutical compositions containing the same, methods of preparing the same, and methods for facilitating the delivery of active agents with the same.

4 Claims, 3 Drawing Sheets

FOREIGN PATENT DOCUMENTS

| | | |
|---|---|---|
| WO | WO-02098453 A2 | 12/2002 |
| WO | WO-03015822 A1 | 2/2003 |
| WO | WO-2004006907 A1 | 1/2004 |
| WO | WO-2004012772 A1 | 2/2004 |
| WO | WO-2005002549 A1 | 1/2005 |
| WO | WO-2005004900 A1 | 1/2005 |
| WO | WO-2005014031 A1 | 2/2005 |
| WO | WO-2006063821 | 3/2006 |
| WO | 2006/063819 * | 6/2006 |
| WO | WO-2006063819 A2 | 6/2006 |

* cited by examiner

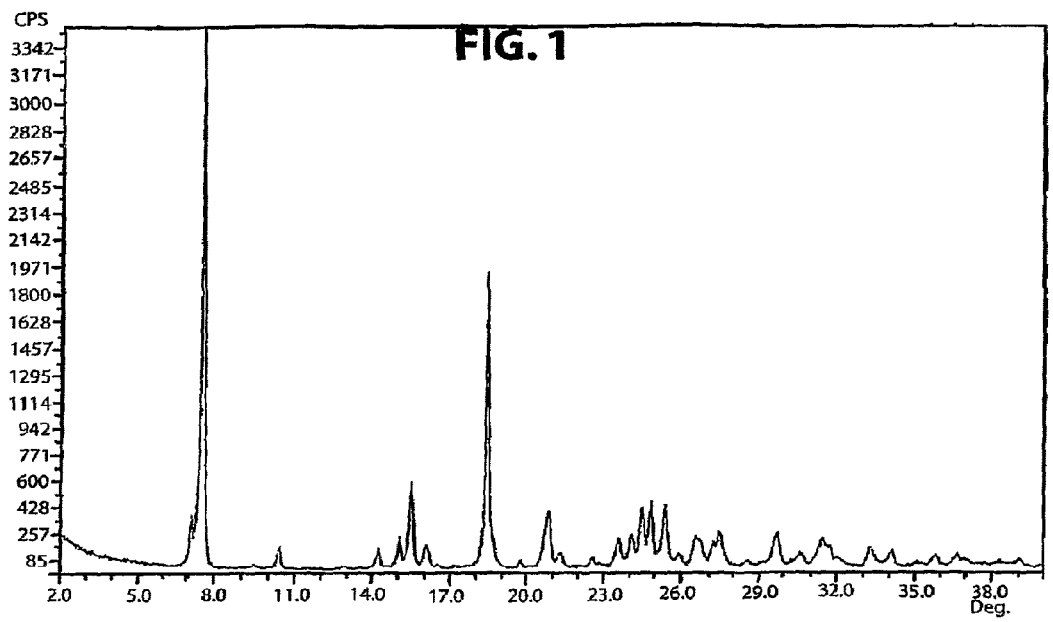
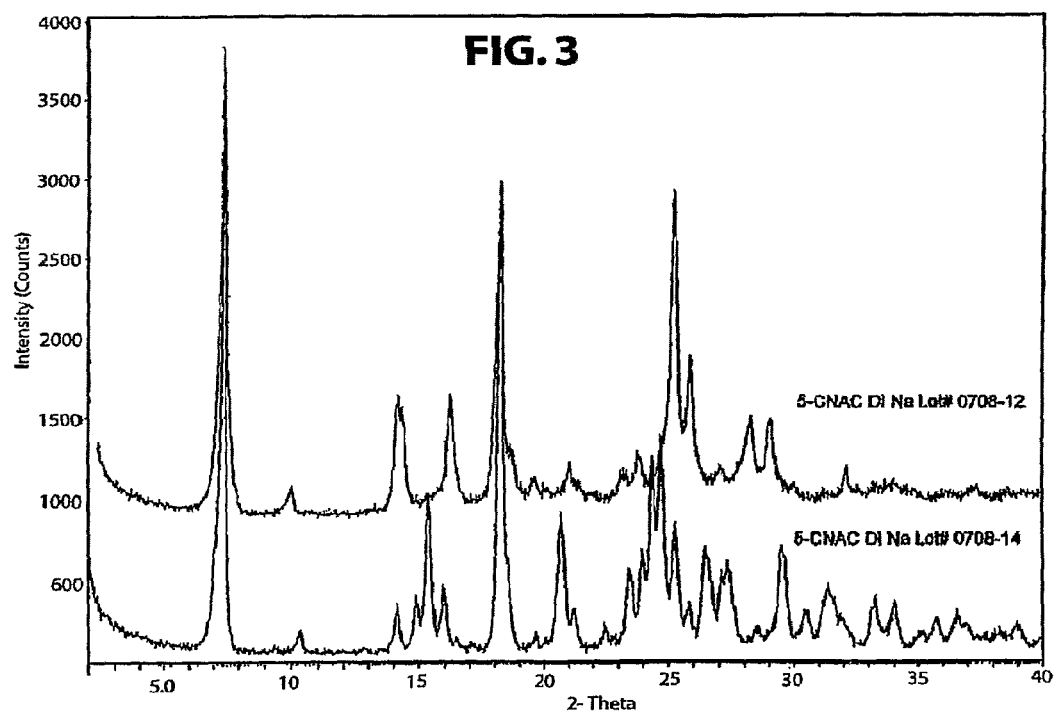

CRYSTALLINE FORMS OF THE DI-SODIUM SALT OF N-(5- CHLOROSALICYLOYL)-8-AMINOCAPRYLIC ACID

This application is a divisional application of U.S. patent application Ser. No. 12/067,239, filed on Jul. 3, 2008, which is a national phase of International Application No. PCT/US2006/036455, filed Sep. 18, 2006, which claims the benefit of U.S. Provisional Application No. 60/718,829, filed Sep. 19, 2005, each of which is hereby incorporated by reference in its entirety.

FIELD OF THE INVENTION

The present invention relates to crystalline forms of the di-sodium salt of N-(5-chlorosalicyloyl)-8-aminocaprylic acid (hereafter "5-CNAC"), pharmaceutical compositions containing the same, methods of preparing the same, and methods for facilitating the delivery of active agents with the same.

BACKGROUND OF THE INVENTION

U.S. Pat. No. 5,773,647 discloses 193 delivery agent compounds, including N-(5-chlorosalicyloyl)-8-aminocaprylic acid ("5-CNAC"). These delivery agent compounds increase the bioavailability of a broad range of biologically active agents, particularly biologically active agents that are not typically amenable to oral administration. U.S. Published Application Nos. 2006/0078622 and 2006/0078623 discloses microparticles or nanoparticles of delivery agent compounds, including 5-CNAC. U.S. Published Patent Application No. 2005/0054557 discloses pharmaceutical compositions that include parathyroid hormone, calcitonin and 5-CNAC. International Publication No. WO 00/59863 discloses the di-sodium salt of N-(5-chlorosalicyloyl)-8-aminocaprylic acid.

International Published Application No. WO 2005/01403 discloses use of calcitonin and 5-CNAC to treat osteoarthritis. U.S. Published Application No. 2006/0106110 discloses a method of inhibiting platelet aggregation in a mammal comprising administering a modified amino acid, including 5-CNAC. International Published Application No. 03/015822 discloses the use of 5-CNAC as an oral delivery agent for parathyroid hormone fragments. International Published Application No. WO 02/45754 discloses pharmaceutical compositions comprising pharmacologically active agents, crospovidone or povidone, and a delivery agent (e.g. 5-CNAC).

SUMMARY OF THE INVENTION

The present invention relates to four crystalline forms of di-sodium salt of N-(5-chlorosalicyloyl)-8-aminocaprylic acid ("5-CNAC") (hereafter referred to as Forms I-IV), including an octahydrate of 5-CNAC.

One embodiment of the invention is a pharmaceutical composition comprising (A) (i) one or more of Forms I-IV of 5-CNAC, and (B) an active agent, such as calcitonin (e.g. salmon calcitonin) or human growth hormone (e.g. recombinant human growth hormone). According to a preferred embodiment, the pharmaceutical composition comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of one of Forms I-IV of 5-CNAC, based upon 100% total weight of 5-CNAC in the pharmaceutical composition. According to another preferred embodiment, the pharmaceutical composition comprises at least about 20, 30, 40, 50, 60, 70, 80, 90, 95, 96, 97, 98, 99, 99.1, 99.2, 99.3, 99.4, 99.5, 99.6, 99.7, 99.8, or 99.9% by weight of one of Forms I-IV of 5-CNAC, based upon 100% total weight of crystalline 5-CNAC in the pharmaceutical composition.

Another embodiment is a pharmaceutical composition, such as a tablet, comprising at least one of Forms I-IV of 5-CNAC and at least one active agent and/or pharmaceutically acceptable additive (such as those described below). A preferred active agent is calcitonin. Yet another preferred active agent is a therapeutic mixture of calcitonin and parathyroid hormone (such as PTH[1-34]). Yet another preferred active agent is insulin. Yet another preferred active agent is growth hormone (such as recombinant human growth hormone).

Yet another embodiment of the invention is a method for administering or facilitating the delivery of an active agent in an animal (such as a human) by administering the pharmaceutical composition of the present invention.

Yet another embodiment is a method of treating Paget's disease or hypercalcemia, or treating or preventing osteoporosis in a mammal (such as a human) in need thereof by orally administering an effective amount of the pharmaceutical composition of the present invention (e.g. a pharmaceutical composition comprising Forms I, II, III, and/or IV of 5-CNAC and (i) calcitonin (e.g. salmon calcitonin) or (ii) a combination of calcitonin and parathyroid hormone or a fragment thereof (such as PTH[1-34]). Other diseases or conditions that may be treated, or physiological affects achieved by orally administering an effective amount of the pharmaceutical composition of the present invention e.g. a pharmaceutical composition comprising Forms I, II, III, and/or IV of 5-CNAC and (i) calcitonin (e.g. salmon calcitonin) or (ii) a combination of calcitonin and parathyroid hormone or a fragment thereof (such as PTH[1-34]) include diseases of the bone, bone pain (including pain associated with osteoporosis or cancer), osteoarthritis, abnormal resportion and turnover of sub-chondral bone, preserving and/or stimulating cartilage, inhibiting phosholipase A2 and/or collagenase activity, stimulating glycosaminoglycan and/or proteoglycan synthesis, stimulating new bone formation, acting on the inhomogeneity in density or stiffness of the subchondral bone, acting on the inflammatory process, leading to attenuations on pain in motion and related symptoms, reducing degenerative change in the joint in a patient.

Yet another embodiment is a method of preparing Form I of 5-CNAC comprising by (a) dissolving a monoethanol solvate of 5-CNAC in a mixture of acetonitrile and water; and (b) cooling the solution prepared in step (a) at an effective temperature (e.g., to from about 5° C. to about 15° C.) to yield Form I of 5-CNAC.

Yet another embodiment is a process for preparing Form I of 5-CNAC by (a) heating an aqueous solution of 5-CNAC (e.g., from about 40° C. to about 70° C.); and (b) removing the water from the solution to yield Form I of 5-CNAC (e.g., with a rotary evaporator and/or vacuum oven).

Yet another embodiment is a process for preparing a monoethanol solvate of 5-CNAC (such as Form II) by (a) adding sodium hydroxide to a solution of N-(5-chlorosalicyloyl)-8-aminocaprylic acid and ethanol; and (b) precipitating Form II of 5-CNAC from the solution. Preferably, the molar ratio of sodium hydroxide to N-(5-chlorosalicyloyl)-8-aminocaprylic acid is about 2:1.

Yet another embodiment is a process for preparing an octahydrate of 5-CNAC (such as Form III) by maintaining (i) a monohydrate of 5-CNAC (such as Form I, IV, or a mixture thereof), (ii) a monoethanol solvate of 5-CNAC (such as Form II), or (iii) a mixture thereof at a relative humidity of at least about 75% for a sufficient dine to form the octahydrate. According to one embodiment, the octahydrate is prepared at ambient temperature or a temperature ranging from about 22° C. to about 40° C. or about 50° C.

Yet another embodiment is a process for preparing Form IV of 5-CNAC by (a) dissolving 5-CNAC in methyl ethyl ketone at an elevated temperature (e.g., from about 30° C. to about 70° C.); and (b) cooling the methyl ethyl ketone solution of step (a) to yield Form IV of 5-CNAC.

Yet another embodiment is a process for preparing a mixture of Forms I and IV of 5-CNAC by cooling a solution of 5-CNAC and acetone for a sufficient time to produce the mixture of Forms I and IV. Optionally, the solution may also contain water.

The crystals prepared by any of the aforementioned procedures may be recovered by any method known in the art.

BRIEF DESCRIPTION OF THE DRAWINGS

FIGS. 1, 3, 4, and 5 are X-ray powder diffractograms (XRPDs) of Forms I-IV of 5-CNAC, respectively, as prepared in Examples 1-4 (The top spectra in FIG. 3 is the spectra for Form II).

DETAILED DESCRIPTION OF THE INVENTION

Definitions

Figure 2:
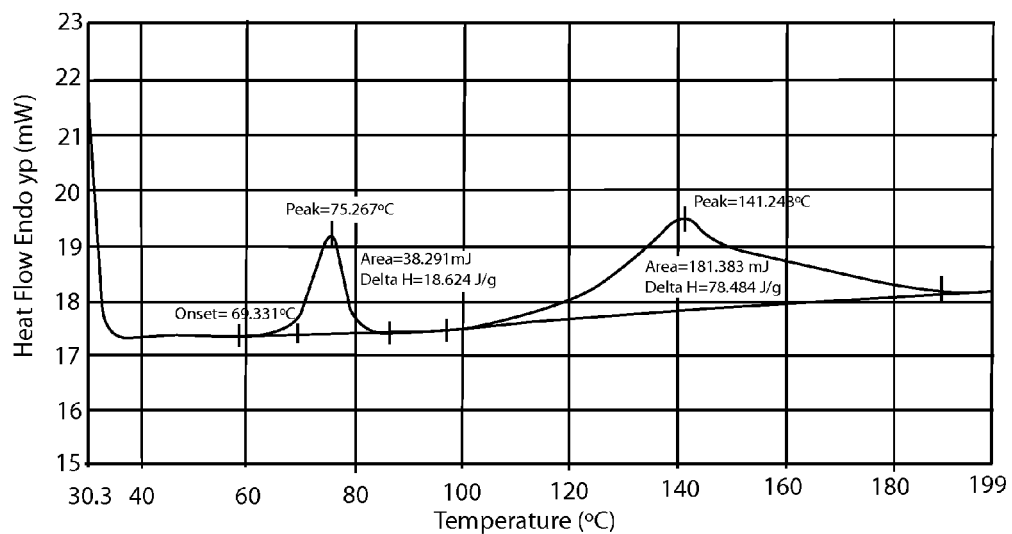
FIGS. 2 and 6 are differential scanning calorimetry (DSC) analyses of Forms I and IV of 5-CNAC, respectively, as prepared in Examples 1 and 4.

The term "polymorph" refers to crystallographically distinct forms of a substance.

The term "hydrate" as used herein includes, but is not limited to, a crystalline substance containing one or more molecules of water in a definite ratio as an integral part of the crystal or a crystalline material containing free water.

The term "5-CNAC" as used herein refers to the disodium salt of N-(5-chlorosalicyloyl)-8-aminocaprylic acid. Unless otherwise noted, the term "5-CNAC" as used herein refers to all polymorphs of 5-CNAC.

The term "5-CNAC monohydrate" as used herein refers to a crystalline form of 5-CNAC in which one molecule of water is associated with each molecule of 5-CNAC.

The term "5-CNAC octahydrate" as used herein refers to a crystalline form of 5-CNAC in which eight molecules of water are associated with each molecule of 5-CNAC.

The term "solvate" as used herein includes, but is not limited to, a molecular or ionic complex of molecules or ions of a solvent with molecules or ions of 5-CNAC. The term "co-solvate" as used herein includes, but is not limited to, a molecular or ionic complex of molecules or ions of two or more solvents with molecules or ions of 5-CNAC.

The term "delivery agent" as used herein refers to 5-CNAC, including its crystalline forms.

An "effective amount of drug" is an amount of the active agent (e.g., heparin, calcitonin, parathyroid hormone, or recombinant human growth hormone) which is effective to treat or prevent a condition in a living organism to whom it is administered over some period of time, e.g., provides a therapeutic effect during a desired dosing interval. Effective doses will vary, as recognized by those skilled in the art, depending on the route of administration, excipients present, and whether the active agent is part of a co-therapy with other agents for treating a condition.

The term "treat", "treating", or "treated" refers to administering an active agent with the purpose to cure, heal, alleviate, relieve, alter, remedy, ameliorate, improve, or affect a condition (e.g., a disease), the symptoms of the condition, or the predisposition toward the condition.

An "effective amount of delivery agent" is an amount of the delivery agent which promotes the absorption of a desired amount of the active agent via any route of administration (such as those discussed in this application including, but not limited to, the oral (e.g., across a biological membrane in the gastrointestinal tract), nasal, pulmonary, dermal, vaginal, and/or ocular route).

The term "calcitonin" as used herein refers to all forms of calcitonin, including, but not limited to, human, salmon, pig and eel calcitonin, including natural, synthetic or recombinant sources thereof, as well as calcitonin derivatives such as 1,7-Asu-eel calcitonin. A preferred calcitonin is synthetic salmon calcitonin.

The term "parathyroid hormone" refers to all forms of parathyroid hormone, natural and synthetic, its fragments and agonists. For example, it may include, but is not limited to, human parathyroid hormone[1-36] and human parathyroid hormone[1-34].

The term "insulin" refers to all forms of insulin, natural and synthetic including, but not limited to, recombinant human insulin.

The term "growth hormone" refers to all forms of growth hormone, natural and synthetic including, but not limited to, human growth hormone (e.g., recombinant human growth hormone).

The term "fragments" of active agents, as used herein, refers to truncated forms of active agent that provides, upon administration to a subject, a similar physiological effect as the non-truncated active agent. The term "analogs" of active agents, as used herein, refers to slightly modified forms of active agent that provides, upon administration to a subject, a similar physiological effect as the active agent from which the analog is based. It is understood that analogs of active agents (e.g. insulin analogs disclosed in U.S. Pat. No. 5,474,978) and fragments of active agents (e.g. the PTH fragments disclosed herein) can be administered with forms I-IV of 5-CNAC with similar efficacy as administration of the active agent (e.g. insulin and PTH) itself with forms I-IV of 5-CNAC.

As used herein, the term "about" means within 10% of a given value, preferably within 5%, and more preferably within 1% of a given value. Alternatively, the term "about" means that a value can fall within a scientifically acceptable error range for that type of value, which will depend on how qualitative a measurement can be given the available tools.

5-CNAC Monohydrate Form I

Form I of 5-CNAC is a monohydrate. Form I is the most stable of Forms I-IV at room temperature. According to differential scanning calorimetry (DSC), Form I has a first endothermic transition with an onset temperature of about 69° C. (69.3° C.) and peaking at about 76° C. (75.2° C.) followed by a second broad endothermic event having an onset temperature of about 98° C. and peaking at about 140° C. (141.2° C.) (see FIG. 2). Form I of 5-CNAC has an XRPD pattern substantially identical to that shown in FIG. 1. For instance, Form I exhibits a characteristic peak at 15.5° 2θ±0.2 or 0.1° 2θ. Characteristic XRPD peak locations (expressed in degrees 2θ±0.2, 0.1, 0.05, or 0.01° 2θ) and d-spacing for Form I are provided in Table 1 below.

TABLE 1

Characteristic XRPD Peaks (expressed in degrees 2θ) of Form I of 5-CNAC

| d-Value (Å) | 2-theta Refraction angle (deg) | Relative Intensity (%) |
|---|---|---|
| 11.788 | 7.5 | 100 |
| 8.507 | 10.4 | 4 |
| 6.238 | 14.2 | 4 |
| 5.907 | 15.0 | 6 |
| 5.717 | 15.5 | 17 |
| 5.506 | 16.1 | 5 |
| 4.822 | 18.4 | 59 |
| 4.271 | 20.8 | 13 |
| 3.770 | 23.6 | 5 |
| 3.693 | 24.1 | 6 |
| 3.634 | 24.5 | 16 |
| 3.590 | 24.8 | 17 |
| 3.507 | 25.4 | 12 |
| 3.351 | 26.6 | 7 |
| 3.279 | 27.2 | 5 |
| 3.244 | 27.5 | 7 |
| 3.018 | 29.6 | 9 |
| 2.840 | 31.5 | 6 |

Form I may be prepared by the procedures described above and in Example 1 below.

The present invention also provides a pharmaceutical composition containing Form I of 5-CNAC in which less than 90, 80, 70, or 60% of the 5-CNAC is crystalline (based on 100% total weight of 5-CNAC).

The present invention also provides a pharmaceutical composition, such as a tablet, comprising a milled (e.g., ball milled) or directly compressed mixture of Form I of 5-CNAC and at least one active agent and/or pharmaceutically acceptable additive (such as those described below). Preferably, the pharmaceutical composition (or milled or directly compressed mixture) includes at least 50, 60, 70, 80, 90, 95, 96, 97, 98, or 99% by weight of Form I based on the total weight of 5-CNAC in the pharmaceutical composition (or milled or directly compressed mixture).

5-CNAC Form II

Form II is a monoethanol solvate of 5-CNAC. Form II of 5-CNAC has an XRPD pattern substantially identical to that shown in FIG. 3. For instance, Form II exhibits a characteristic peak at 16.5° 2θ±0.2 or 0.1° 2θ. Characteristic XRPD peak locations (expressed in degrees 2θ±0.2, 0.1, 0.05, or 0.01° 2θ) and d-spacing for Form II are provided in Table 2 below.

TABLE 2

Characteristic XRPD Peaks (expressed in degrees 2θ) of Form II of 5-CNAC

| d-Value (Å) | 2-theta refraction angle |
|---|---|
| 11.788 | 7.5 |
| 6.282 | 14.1 |
| 5.373 | 16.5 |
| 4.796 | 18.5 |
| 3.562 | 25 |
| 3.427 | 26 |

Form II of 5-CNAC may be prepared as described above and in Example 2.

5-CNAC Octahydrate Form III

Form III is an octahydrate of 5-CNAC. Form III is unstable at a relative humidity below about 50%. Form III of 5-CNAC has an XRPD pattern substantially identical to that shown in FIG. 4. For instance, From III exhibits a characteristic peak at 4.8° 2θ±0.2 or 0.1° 2θ. Characteristic XRPD peak locations (expressed in degrees 2θ±0.2, 0.1, 0.05, or 0.01° 2θ) and d-spacing for Form III are provided in Table 3 below.

TABLE 3

Characteristic XRPD Peaks (expressed in degrees 2θ) of Form III of 5-CNAC

| d-Value (Å) | 2-theta Refraction angle (deg) | Relative Intensity (%) |
|---|---|---|
| 18.412 | 4.8 | 100 |
| 8.507 | 10.4 | 6 |
| 7.564 | 11.7 | 11 |
| 6.068 | 14.6 | 32 |

Form III may be prepared as described above and in Example 3. For example, Form III can be made by storing disodium 5-CNAC (such as its ethanol solvate) at 75% relative humidity (or higher) for at least six days.

The present invention also provides a pharmaceutical composition, such as a tablet, comprising a directly compressed mixture of Form III of 5-CNAC and at least one active agent and/or pharmaceutically acceptable additive (such as those described below). Preferably, the pharmaceutical composition (or directly compressed mixture) includes at least 50, 60, 70, 80, 90, 95, 96, 97, 98, or 99% by weight of Form III based on the total weight of 5-CNAC in the pharmaceutical composition (or directly compressed mixture).

5-CNAC Monohydrate Form IV

Form IV of 5-CNAC is a monohydrate. Form IV of 5-CNAC has an XRPD pattern substantially identical to that shown in FIG. 5. For instance, From IV exhibits a characteristic peak(s) at 7.2° and/or 18.2° 2θ±0.2 or 0.1° 2θ. Characteristic XRPD peak locations (expressed in degrees 2θ±0.2, 0.1, 0.05, or 0.01° 2θ) and d-spacing for Form IV are provided in Table 4 below.

TABLE 4

Characteristic XRPD Peaks (expressed in degrees 2θ) of Form IV of 5-CNAC

| d-Value (Å) | 2-theta Refraction angle (deg) | Relative Intensity (%) |
|---|---|---|
| 12.279 | 7.2 | 52 |
| 4.875 | 18.2 | 100 |
| 3.605 | 24.7 | 7 |

Form IV may be prepared as described above and in Example 4.

The present invention also provides a pharmaceutical composition containing Form IV of 5-CNAC in which at least 50, 60, 70, 80 or 90% of the 5-CNAC is crystalline based on 100% weight of 5-CNAC.

Mixture of 5-CNAC Forms I and IV

Forms I and IV of 5-CNAC are monohydrates. Characteristic XRPD peak locations (expressed in degrees 2θ±0.2, 0.1, 0.05, or 0.01° 2θ) and d-spacing for the mixture are provided in Table 5 below.

TABLE 5

Characteristic XRPD Peaks (expressed in degrees 2θ) of Mixture of Forms I and IV of 5-CNAC

| d-Value (Å) | 2-theta Refraction angle | Relative Intensity |
| --- | --- | --- |
| 12.452 | 7.1 | 9 |
| 11.788 | 7.5 | 100 |
| 8.507 | 10.4 | 4 |
| 6.238 | 14.2 | 3 |
| 5.907 | 15.0 | 5 |
| 5.717 | 15.5 | 16 |
| 5.506 | 16.1 | 4 |
| 4.822 | 18.4 | 60 |
| 4.251 | 20.9 | 11 |
| 3.770 | 23.6 | 4 |
| 3.693 | 24.1 | 5 |
| 3.634 | 24.5 | 10 |
| 3.576 | 24.9 | 11 |
| 3.507 | 25.4 | 11 |
| 3.351 | 26.6 | 5 |
| 3.279 | 27.2 | 4 |
| 3.244 | 27.5 | 6 |
| 3.008 | 29.7 | 6 |
| 2.840 | 31.5 | 5 |

The mixture can be prepared as described above and in Example 5.

The crystals prepared by any of the aforementioned procedures may be recovered by any method known in the art.

Active Agents

Active agents suitable for use in the present invention include biologically active agents and chemically active agents, including, but not limited to, pesticides, pharmacological agents, and therapeutic agents. Suitable active agents include those that are rendered less effective, ineffective or are destroyed in the gastro-intestinal tract by acid hydrolysis, enzymes and the like. Also included as suitable active agents are those macromolecular agents whose physiochemical characteristics, such as, size, structure or charge, prohibit or impede absorption when dosed orally.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e., polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone releasing hormones; growth hormone releasing factor, interferons, including α (e.g., interferon alfacon-1 (available as Infergen® from InterMune, Inc. of Brisbane, Calif.)), β and γ, interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; anti-migraine agents such as BIBN-4096BS and other calcitonin gene-related proteins antagonists; glucagon-like peptide 1 (GLP-1); Argatroban; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

According to one embodiment, the active agent is a pharmacologically active peptide, such as a bone active agent (e.g. calcitonin). Bone active agents include classes of agents which display in vivo pharmacological activity in animals such as stabilization, healing, or growth of bone, deceleration or inhibition of bone turnover, deceleration or inhibition of bone resorption, inhibition of osteoclast activity, and stimulation of osteoblast activity. Some of these agents may be peptidic, for example, calcitonins, parathyroid hormone (PTH), PTH fragments (e.g., PTH[1-34]), Transforming Growth Factors(TGFs), and analogs and fragments of any of the above. The bone active agents may also be small molecule non-peptidic structures which show in vivo pharmacological bone activities as described above in this paragraph.

A known class of such pharmacologically active agents, calcitonins, have varying pharmaceutical utility and are commonly employed in the treatment of, e.g., Paget's disease, hypercalcemia and osteoporosis (including, but not limited to, postmenopausal osteoporosis). Various calcitonins, including salmon, pig and eel calcitonin are commercially available and commonly employed for the treatment of, e.g., Paget's disease, hypercalcemia of malignancy and osteoporosis. The calcitonin can be any calcitonin (e.g., human, salmon, pig or eel), including natural, synthetic or recombinant sources thereof, as well as calcitonin derivatives such as 1,7-Asu-eel calcitonin. The compositions can comprise a single calcitonin or any combination of two or more calcitonins. The preferred calcitonin is synthetic salmon calcitonin.

The calcitonins are commercially available or may be synthesized by known methods.

When the pharmacologically active agent is salmon calcitonin, the appropriate dosage will, of course, vary depending upon, for example, the host and the nature and severity of the condition being treated. Suitable dosage amounts are provided in International Publication Nos. WO 2004/012772, WO 2005/004900, and WO 2005/014031, all of which are hereby incorporated by reference. An oral human dose of salmon calcitonin is typically in the range of about 0.05 mg-5 mg, preferably about 0.1 mg-2.5 mg, when administered in combination with an oral delivery agent (e.g. 5-CNAC). According to one embodiment, from about 0.4 mg to about 2.5 mg of salmon calcitonin is administered daily to a patient, e.g., a human such as an average human of about 70 kg. More preferably, from about 0.8 to about 1.2 mg, e.g., about 1 mg, is administered daily. Also preferred are doses less than 1 mg but higher than 0.4 mg.

Suitable dosage amounts of parathyroid hormone are provided in International Publication Nos. WO 2005/002549, WO 03/015822, and WO 02/098453, all of which are hereby incorporated by reference. The amount of parathyroid to be administered is an amount effective to achieve the physiological conditions desired. In one embodiment the amount of parathyroid component (e.g., PTH, PTH[1-28]-PTH[1-41]) is such that it provides a daily administered dose of PTH component of from about 0.001 µg/kg to about 10 mg/kg of animal body weight, or from about 1 µg/kg to about 6 µg/kg of animal body weight. Unit dosage forms may contain, for example, 800 µg of PTH component. Particular PTH amounts for specific applications will vary according to the age, size, sex and condition of the subject to be treated and can be determined by persons of ordinary skill in the art.

Amounts of HGH or HGH component can also be determined by persons of ordinary skill in the art. In one embodiment, the amount of HGH (e.g. the 191 amino acid native species (somatropin)) or HGH component (e.g. the 192 amino acid N-terminal methionine (met) species (somatrem)) is such that it provides in a unit dosage form of from about 10 mg to about 300 mg of HGH or HGH component (e.g. 100 mg of HGH or HGH component). Particular HGH amounts for specific applications will vary according to the age, size, sex and condition of the subject to be treated and can be determined by persons of ordinary skill in the art.

The pharmacologically active agent generally comprises from about 0.05 percent to about 70 percent by weight relative to the total weight of the overall pharmaceutical composition, preferably an amount of from about 0.01 percent to about 50 percent by weight, more preferably about 0.3 percent to about 30 percent by weight relative to the total weight of the overall pharmaceutical composition.

Pharmaceutical Compositions

The pharmaceutical composition is preferably in solid form and may be in the form of a dosage form (e.g. a solid dosage form, such as a solid oral dosage form). The solid dosage form can be a capsule, tablet or particle, such as a powder or sachet. The powder may be in the form of a sachet that is mixed with a liquid and administered. Also the powder can also be packed into capsules or pressed into tablets, or the powder may be administered to the subject as-is.

Alternatively, the solid dosage form can be a topical delivery system, such as an ointment, cream or semi-solid. For example, the powders may be added to topical excipients (e.g. polyethylene glycol) and administered as an ointment.

The pharmaceutical composition can include a sustained release or controlled release system. Preferably, the solid dosage form is for oral administration.

The amount of delivery agent in the solid dosage form is a delivery effective amount and can be determined for any particular compound or biologically or chemically active agent by methods known to those skilled in the art.

Following administration, the active agent in the dosage unit form is taken up into circulation. The bioavailability of the active agent is readily assessed by measuring a known pharmacological activity in blood, e.g., an increase in blood clotting time caused by heparin, or a decrease in circulating calcium levels caused by calcitonin. Alternately, the circulating levels of the active agent itself can be measured directly.

The solid dosage form may include pharmaceutically acceptable additives, such as excipients, carriers, diluents, stabilizers, plasticizers, binders, glidants, disintegrants, bulking agents, lubricants, plasticizers, colorants, film formers, flavoring agents, preservatives, dosing vehicles, surfactants, and any combination of any of the foregoing. Preferably, these additives are pharmaceutically acceptable additives, such as those described in *Remington's, The Science and Practice of Pharmacy*, (Gennaro, A. R., ed., 19th edition, 1995, Mack Pub. Co.) which is herein incorporated by reference.

Suitable binders include, but are not limited to, starch, gelatine, sugars (such as sucrose, molasses and lactose), dibasic calcium phosphate dihydrate, natural and synthetic gums (such as acacia, sodium alginate, carboxymethyl cellulose, methyl cellulose, polyvinylpyrrolidone, polyethylene glycol, ethylcellulose, and waxes.

Suitable glidants include, but are not limited to, talc, and silicon dioxide (silica) (e.g, fumed silica and colloidal silicon dioxide).

Suitable disintegrants include, but are not limited to, starches, sodium starch glycolate, croscarmellose sodium, crospovidone, clays, celluloses (such as purified cellullose, methylcellulose, sodium carboxymethyl cellulose), alginates, pregelatinized corn starches, and gums (such as agar, guar, locust bean, karaya, pectin and tragacanth gums). A preferred disintegrant is sodium starch glycolate.

Suitable bulking agents include, but are not limited to, starches (such as rice starch), microcrystalline cellulose, lactose (e.g., lactose monohydrate), sucrose, dextrose, mannitol, calcium sulfate, dicalcium sulfate, and tricalcium sulfate.

Suitable lubricants include, but are not limited to, stearic acid, stearates (such as calcium stearate and magnesium stearate), talc, boric acid, sodium benzoate, sodium acetate, sodium fumarate, sodium chloride, polyethylene glycol, hydrogenated cottonseed, and castor oils.

Suitable surfactants include, but are not limited to, sodium lauryl sulfate, hydroxylated soy lecithin, polysorbates, and block copolymers of propylene oxide and ethylene oxide.

The pharmaceutically acceptable inactive excipients may include polymers and inactive compounds which for example, aid the formulation or manufacturing of the solid oral dosage form contemplated by the present invention or which may aid the release of the solid oral composition in the gastro-intestinal environment.

In an additional embodiment of the present invention the pharmaceutically acceptable inactive excipient may be either or both of the polymers crospovidone or povidone.

The pharmaceutical inactive ingredients, referred to above, for example optionally include crospovidones and povidones, which may be any crospovidone and povidone. Crospovidone is a synthetic crosslinked homopolymer of N-vinyl-2-pyrrolidone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation. The preferred crospovidone is Polyplasdone XL.

Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP.

As mentioned above, the crospovidones and povidones are commercially available. Alternatively, they may be synthesized by known processes.

The crospovidone, povidone or combination thereof is generally present in the compositions in an amount of from about 0.5 percent to 50 percent by weight relative to the total weight of the overall pharmaceutical composition, preferably an amount of from 2 percent to 25 percent, more preferably 5 percent to 20 percent by weight relative to the total weight of the pharmaceutical composition.

Delivery Systems

The amount of active agent used in a pharmaceutical composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than other compositions or compositions containing the active agent alone, lower amounts of biologically or chemically active agents than those used in prior dosage unit forms or delivery systems can be administered to the subject, while still achieving the same blood levels and/or therapeutic effects.

Generally, the weight ratio of delivery agent (e.g. 5-CNAC) to active agent (e.g. HGH or HGH component, PTH or PTH fragment) ranges from about 0.1:1 to about 300:1 or 1000:1. In one embodiment the weight ratio of delivery agent (e.g. 5-CNAC) to active agent (e.g. HGH or HGH component, PTH or PTH fragment) ranges from about 50:1 or 40:1 to about 0.5: or 0.2:1. In one embodiment the weight ratio of delivery agent (e.g. 5-CNAC) to active agent (e.g. HGH or HGH component, PTH or PTH fragment) ranges from about 10:1 to about 0.5:1 (e.g. 2:1). The weight ratio of delivery agent (e.g. 5-CNAC) is calculated based on the free acid form of the delivery agent. The weight ratio will vary according to the active agent and the particular indication for which the active agent is administered.

The presently disclosed delivery agents facilitate the delivery of biologically and chemically active agents, particularly in oral, sublingual, buccal, intraduodenal, intracolonic, rectal, vaginal, mucosal, pulmonary, intranasal, and ocular systems.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The compounds and compositions are particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference ($59^{th}$ Ed., 2005, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
| --- | --- |
| Growth hormones (including human recombinant growth hormone and growth-hormone releasing factors and its analogs) | Growth disorders; preventing muscle wasting |
| Interferons, including $\alpha$, $\beta$ and $\gamma$ | Viral infection, including chronic cancer, hepatitis, and multiple sclerosis |
| Interleukins (e.g. Interleukin-1; interleukin-2) | Viral infection; cancer; cell mediated immunity; and transplant rejection; |
| Insulin; Insulin-like growth factor IGF-1 | Diabetes |
| Immune Globulins, such as IVIg | smallpox, rabies, and diphtheria, Alzheimer's Disease; Primary immunodeficiencies; Acute Guillain-Barré syndrome; Chronic idiopathic demyelinating polyneuropathy (CIDP); Myasthenia gravis, polymyositis, and dermatomyositis; neonatal immune thrombocytopenia, heparin-induced thrombocytopenia, and antiphospholipid antibody syndrome: Posttransfusion purpura. |
| Heparin | Treatment and Prevention of Thrombosis, including (Deep Vein Thrombosis); prevention of blood coagulation |
| Calcitonin | Osteoporosis; diseases of the bone; bone pain; analgesic (including pain associated with osteoporosis or cancer) |
| Erythropoietin, Pegylated erythropoietin. | Anemia; HIV/HIV-therapy Associated Anemia; Chemotherapeutically-Induced Anemia |
| Atrial naturetic factor | Vasodilation |
| Antigens | Infection |
| CPHPC | Reduction of amyloid deposits and systemic amyloidoisis often (but not always) in |

-continued

| Active Agent | Disease and Physiological Effect |
|---|---|
| | connection with Alzheimer's disease, Type II diabetes, and other amyloid-based diseases |
| Monoclonal antibodies | To prevent graft rejection; cancer; used in assays to detect diseases |
| Somatostatin/octreotide | Bleeding ulcer; erosive gastritis; variceal bleeding; diarrhea; acromegaly; TSH-secreting pituitary adenomas; secretory pancreatic tumors; carcinoid syndrome; reduce proptosis/thyroid-associated ophthalmopathy; reduce macular edema/retinopathy; decreases growth hormone and insulin-like growth factor |
| Protease inhibitors | HIV Infection/AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; Leutinizing Hormone; follicle stimulating hormone | Regulate reproductive function |
| Glucocerebrosidase | Gaucher disease (to metabolize lipoprotein) |
| Thrombopoietin | Thrombocytopenia |
| Filgrastim (Granulocyte Colony Stimulating Factor); GM-CSF, (sargramostim) and their Pegylated forms | shorten the duration of chemotherapy-induced neutropenia and thus treat or prevent infection in chemotherapy patients; Inhibit the growth of or to kill Mycobacterium Intracellular Avium Infection (MAC) |
| RNAi | Huntington, Alzheimers, Viral Infections (HIV, Hepatitis A, B or C, RSV), Cancers; Macular Degeneration |
| Prostaglandins | Hypertension |
| Cyclosporin | Transplant rejection; psoriasis, inflammatory alopecias; Sjogren's syndrome; Keratoconjunctivitis Sicca |
| Vasopressin | Nocturnal Enuresis; antidiuretic |
| Cromolyn sodium; | Asthma; allergies |
| Vancomycin | Treat or prevent antimicrobial-induced infections including, but not limitted to methacillin-resistant Staphalococcus aureus and Staph. epidermiditis |
| gallium salts (such as gallium nitrate) | Osteoporosis; Paget's disease; Inhibits osteoclasts; Promotes osteoblastic activity, hypercalcemia, including cancer related hypercalcemia, urethral (urinary tract) malignancies; anti-tumors, cancers, including urethral and bladder cancers; lymphoma; malignancies (including bladder cancer); leukemia; management of bone metastases (and associated pain); muliple myeloma, attenuate immune response, including allogenic transplant rejections; disrupt iron metabolism; promote cell migration; wound repair; to attenuate or treat infectious processes of mycobacterium species, including but not limited to mycobacterium tubercolosis, and mycobacterium avium complex |
| Desferrioxamine (DFO) | Iron overload |
| Parathyroid hormone (PTH), including its fragments. | Osteoporosis; Diseases of the bone |
| Antimicrobials | Infection including but not limited to gram-positive bacterial infection |
| Vitamins | Treat and prevent Vitamin deficiencies |
| Bisphosphonates | Osteoporosis; Paget's disease; bone tumors and metastases (and associated pain); Breast cancer; including as adjuvant therapy for early stage breast cancer; management of bone metastases (and associated pain), including bone metastases associate with breast cancer, prostate cancer, and lung cancer; Inhibits osteoclasts; Promotes osteoblastic activity; treat and/or prevent bone mineral density (bmd) loss; multiple myeloma; prevention of bone complications related to malignant osteolysis; fibrous dysplasia; pediatric osteogenesis imperfecta; hypercalcemia, urethral (urinary tract) malignancies; reflex sympathetic dystropy synodrome, acute back pain after vertebral crush fracture, chronic inflammatory joint disease, renal bone disease, extrosseous |

-continued

| Active Agent | Disease and Physiological Effect |
|---|---|
| | calcifications, analgesic, vitamin D intoxication, periarticular ossifications |
| BIBN4096BS-(1-Piperidinecarboxamide. N-[2-[[5-amino-1-[[4-(4-pyridinyl)-1-piperazinyl)carbonyl]pentyl]amino]-1-[(3,5-dibromo-4-hydroxyphenyl)methyl]-2-oxoethyl]-4(1,4-dihydro-2-oxo-3(2H0-quinazolinyl)-.[R—(R*,S*)]-) | Anti-migraine; calcitonin gene-related peptide antagonist |
| Glucagon | improving glycemic control (e.g. treating hypoglycemia and controlling hypoglycemic reactions), obesity; a diagnostic aid in the radiogical examination of the stomach, duodenum, small bowel and colon; Treat acute poisoning With Cardiovascular Agents including, but not limited to, calcium channel blockers, beta blockers |
| GLP-1, Exendin-3, Exendin-4, Obestatin | Diabetes; improving glycemic control (e.g. treating hypoglycemia and controlling hypoglycemic reactions), obesity |
| dipeptidyl peptidase IV (DPP-4) inhibitors | Diabetes; improving glycemic control (e.g. treating hypoglycemia), obesity |
| acyclovir, valacyclovir | Used to treat herpes infections of the skin, lip and genitals; herpes zoster (shingles); and chickenpox |
| HIV Entry Inhibitors (e.g. Fuzeon) | Inhibit entry of HIV into host cells |
| Sumatriptin, almotriptan, naratriptan, rizatriptan, frovatriptan and eletriptan (piperidinyloxy)phenyl, (piperidinyloxy)pyridinyl, (piperidinylsulfanyl)phenyl and (piperidinylsulfanyl)pyridinyl compounds | anti-migraine serotonin agonists |
| Neuraminidase inhibitors: peramivir, zanamivir, oseltamivir, BCX-1898, BCX-1827, BCX-1989, BCX 1923, BCX 1827 and A315675; M2 inhibitors: amantadine, rimantadine; Nucleoside/Nucleotide Reverse Transcriptase Inhibitors, Non-nucleoside Reverse Transcriptase Inhibitors, Protease Inhibitors, Fusion inhibitors: thiovir, thiophosphonoformate, foscarnet, enfuviritide, zidovudine, didanosine, zalcitabine, stavudine, lamivudine, emtricitabine, abacavir, azidothymidine, tenofovir disoproxil, delavridine, efavirenz, nevirapine, ritonavir, nelfinavir mesylate, saquinvir mesylate, indinavir sulfate, amprenavir, lopinavir, lopinavir, fosamprenavir calcium, atazanavir sulfate | Antivirals |
| Peptide YY (PYY) and PYY-like Peptides (e.g. PYY[3-36]) | Obesity, Diabetes, Eating Disorders, Insulin-Resistance Syndromes |
| Apo a-1 and its mimetics (e.g. APP018) | Decreases HDL; treats or prevents atherosclerosis, treats hypercholesterolemias |
| Imitinab | Used to treat chronic myeloid leukemia, and gastrointestinal stromal tumors |
| influenza virus vaccine, types A and B (surface antigen) | Prevents influenza infections |
| ranibizumab | To treat or prevent macular degeneration (e.g., wet macular degeneration and age-related macular degeneration) |

Another embodiment is a method of treating a disorder responsive to the action of calcitonin, such as Paget's disease, hypercalcemia or osteoporosis (e.g. treating postmenopausal osteoporosis in women greater than five years postmenopause with low bone mass relative to healthy premenopausal women), in a mammal (e.g., a human) in need thereof by orally administering a pharmaceutical composition of the present invention which contains Forms I, II, III and/or IV of 5-CNAC and calcitonin. Preferably, the pharmaceutical composition is administered in the absence of food, advantageously a short interval prior to the consumption of food, for instance, a short interval before a meal, so as to enhance the oral bioavailability of calcitonin.

Another embodiment is a method of treating a disorder responsive to the action of human growth hormone, such as growth disorders (e.g. short stature), in a mammal (e.g., a human) in need thereof by orally administering a pharmaceutical composition of the present invention which contains Forms I, II, III and/or IV of 5-CNAC and human growth hormone. Other examples of conditions that can be treated, or effects achieved with pharmaceutical compositions of the present invention that include Forms I, II, III and/or IV of 5-CNAC and human growth hormone include long-term treatment of pediatric patients who have growth failure due to an inadequate secretion of endogenous growth hormone, long-term treatment of pediatric patients who have growth failure due to Prader-Willi syndrome (PWS), short stature associated with Turner syndrome in patients whose epiphyses are not closed, idopathic short stature, long term replacement therapy in adults with growth hormone deficiency (GHD) of either childhood or adult-onset etiology (e.g. growth hormone deficiencies as a result of pituitary disease, hypothalamic disease, surgery, radiation therapy, chronic renal insufficiency or trauma), and long-term treatment of growth failure in children born small for gestational age who fail to manifest catch-up growth by age 2.

Another embodiment is a method of treating a disorder responsive to the action of parathyroid hormone, such as osteoporosis (e.g. postmenopausal women with osteoporosis who are at high risk for fracture), in a mammal (e.g., a human) in need thereof by orally administering a pharmaceutical composition of the present invention which contains Forms I, II, III and/or IV of 5-CNAC and parathyroid hormone. Other examples of conditions that can be treated, or effects achieved with pharmaceutical compositions of the present invention that include Forms I, II, III and/or IV of 5-CNAC and parathyroid hormone include increase in bone mass in men with primary or hypogonadal osteoporosis who are at high risk for fracture.

Another embodiment is a method of treating a disorder responsive to the action of Imitinab, such as chronic myeloid leukemia, and gastrointestinal stromal tumors, in a mammal (e.g., a human) in need thereof by orally administering a pharmaceutical composition of the present invention which contains Forms I, II, III and/or IV of 5-CNAC and Imitinab.

Another embodiment is a method of treating a disorder responsive to the action of influenza virus vaccine, such as influenza infections, in a mammal (e.g., a human) in need thereof by orally administering a pharmaceutical composition of the present invention which contains Forms I, II, III and/or IV of 5-CNAC and influenza virus vaccine.

Another embodiment is a method of treating a disorder responsive to the action of ranibizumab, such as macular degeneration (e.g., wet macular degeneration and age-related macular degeneration), in a mammal (e.g., a human) in need thereof by orally administering a pharmaceutical composition of the present invention which contains Forms I, II, III and/or IV of 5-CNAC and ranibizumab.

The following examples illustrate the present invention without limitation. All percentages are by weight unless otherwise specified.

DSC

The melting points cited were determined by differential scanning calorimety (DSC). The quoted values were obtained with a Perkin Elmer Differential Scanning Calorimeter DSC-7. The DSC curves were recorded using a heating rate of 20 K/min and a sample mass of 1-3 mg.

XRPD

The Powder X-Ray diffraction analysis was done using a Scintag X1 diffractometer and copper $K\alpha_1$ radiation.

Example 1

Preparation of Form I of 5-CNAC

Form I of 5-CNAC was prepared as follows. A 200 gallon glass-lined reactor was set up for atmospheric distillation. Cooling was applied to the condenser and receiver. The reactor was purged with nitrogen. The reactor was charged with 565 L of acetonitrile. The agitator was set at 100 rpm. The reactor was charged with 13.7 kg of purified water and 43.25 kg of 5-CNAC monoethanol solvate. The reactor contents were heated to reflux causing distillate to begin collecting in the receiver. Atmospheric distillation was continued until approximately 102 L of distillate was collected. Heating of the reactor jacket was stopped and a mixture of 102 L of fresh acetonitrile and 2.5 kg of purified water were charged to the reactor. The reactor contents were cooled to between 5 and 15° C. and agitate for between one and two hours. The resultant slurry was isolated by centrifugation. The wet cake was not washed. The wet cake was dried in a vacuum oven at full vacuum between 75 and 85° C. for 48 hours. The yield of disodium 5-CNAC monohydrate was approximately 40 kg for a yield of about 99.9%.

XRPD and DSC spectra for Form I as prepared above are shown in FIGS. 1 and 2, respectively.

Example 1A

Preparation of Form I of 5-CNAC

Form I was also prepared as follows. A 22 L, Pyrex glass, five-neck, round bottom flask was equipped with an overhead stirrer, thermocouple temperature read out, and heating mantle. The flask was charged with 2602.3 g of 5-CNAC and 4000 mL water. To this stirred slurry was added a solution of 660 g of sodium hydroxide dissolved in 2000 mL water. The mixture was heated to 55° C. and most of the solids dissolved. The slightly hazy solution was hot filtered through Whatman #1 filter paper to remove the insoluble particulates. The filtrate was transferred to the pot flask of a large laboratory rotary evaporator. The rotary evaporator was operated with a bath temperature of 60° C. and a pressure of 60 mmHg. Water was removed from the disodium salt solution until a solid mass was obtained in the rotary evaporator pot flask. The vacuum was released and pot flask removed from the rotary evaporator. The solids were scraped from the pot flask into trays. These trays were then placed in a vacuum oven and the solids dried at 60° C. and full vacuum for 48 hours. The dried solids were run through a laboratory mill until all the solids passed through a 35 mesh screen. The milled and sieved disodium 5-CNAC monohydrate was put into trays and placed back into the drying oven. Drying was continued at 45° C. and full vacuum giving 2957.1 g of the desired product as a dry powder.

Example 2

Preparation of Form II of 5-CNAC

Form II of 5-CNAC was prepared as follows. Into a 200 gallon stainless steel reactor was charged 132 L of ethanol and 11.6 kg of sodium hydroxide pellets. The reactor was heated to about 55° C. and held at this temperature until the sodium hydroxide dissolved. The sodium hydroxide/ethanol solution was cooled and maintained at a temperature of at least 25° C. The sodium hydroxide/ethanol solution was sampled for base assay by titration. Into a second 200 gallon glass-lined reactor was charged 135 L of ethanol and 44.69 kg of 5-CNAC. The slurry was heated to 55° C. with agitation. This temperature and agitation were maintained until the solids dissolved. Two molar equivalents (as determined by titration assay) of the ethanol/sodium hydroxide solution were added to the stirred ethanol/5-CNAC solution. The disodium 5-CNAC ethanol solvate began to precipitate as the sodium hydroxide solution was added. This addition step was exothermic and had to be controlled to prevent excessive reflux. The reactor was set up for atmospheric distillation and about 146 L of ethanol was distilled off. The batch was cooled to less than 10° C. and held at this temperature for at about 4 hours. The solid product was recovered by centrifuge filtration. The filter cake was placed in a drying oven and dried at 45° C. and full vacuum for between about 16 and 24 hours. The yield of dried disodium 5-CNAC monoethanol solvate was about 43.25 kg.

The XRPD spectrum for Form II is shown in FIG. 3.

Example 3

Preparation of Form III of 5-CNAC

Form III was prepared as follows. A thin layer of disodium 5-CNAC monoethanol solvate was spread in a glass tray. The tray containing the material was placed in a 40° C. humidity chamber set at 75% RH. The solids in the glass tray were periodically stirred and weighed. The material was left in the humidity chamber until the sample no longer changed weight or contained ethanol as determined by gas chromatography. This took about six days.

Figure 4:
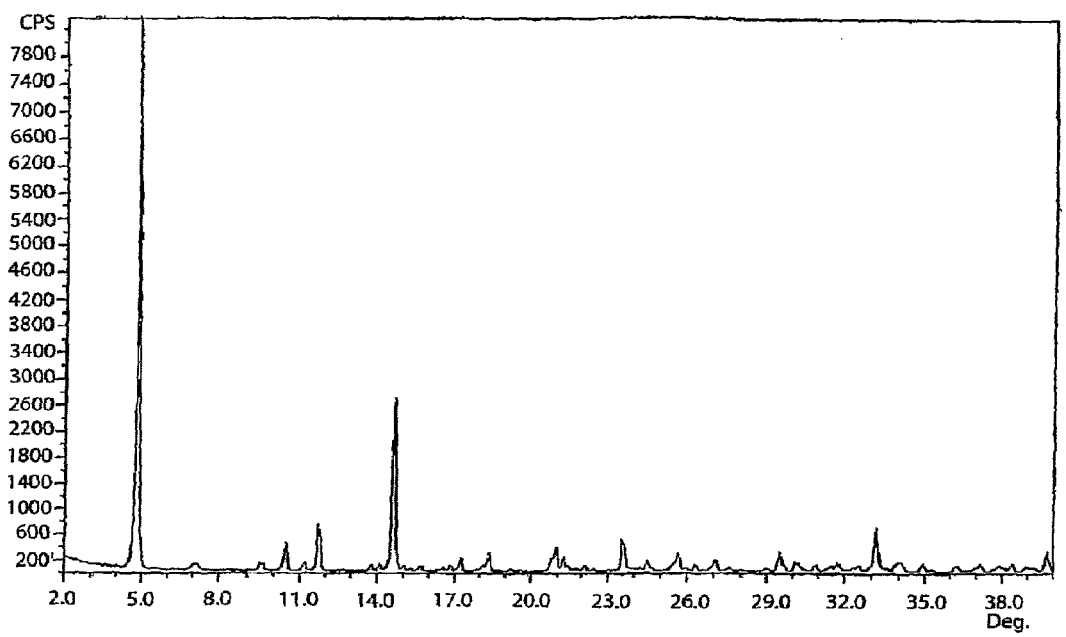

The XRPD spectrum for Form III is shown in FIG. 4.

Example 4

Preparation of Form IV of 5-CNAC

Form IV was prepared as follows. A one liter reactor equipped with a bottom drain was charged with 375 mL of 2-butanone, 125 mL water, and 125 g of disodium 5-CNAC monohydrate. The reactor contents were agitated and heated to 50° C. The solids dissolved resulting in a biphasic solution. The agitation was stopped and the solution allowed to separate into two immiscible liquid layers. The bottom drain on the reactor was used to remove and discard the lower layer. The remaining solution was cooled to ambient temperature. The product began to crystallize during this cooling cycle. To the resulting slurry was added 250 mL of extra 2-butanone. The solid product was recovered by vacuum filtration through a sintered glass funnel. The wet cake was dried overnight in a 55° C. vacuum oven at full vacuum. The dry disodium 5-CNAC monohydrate had a weight of 54.35 g. The yield was 43%.

Figure 6:
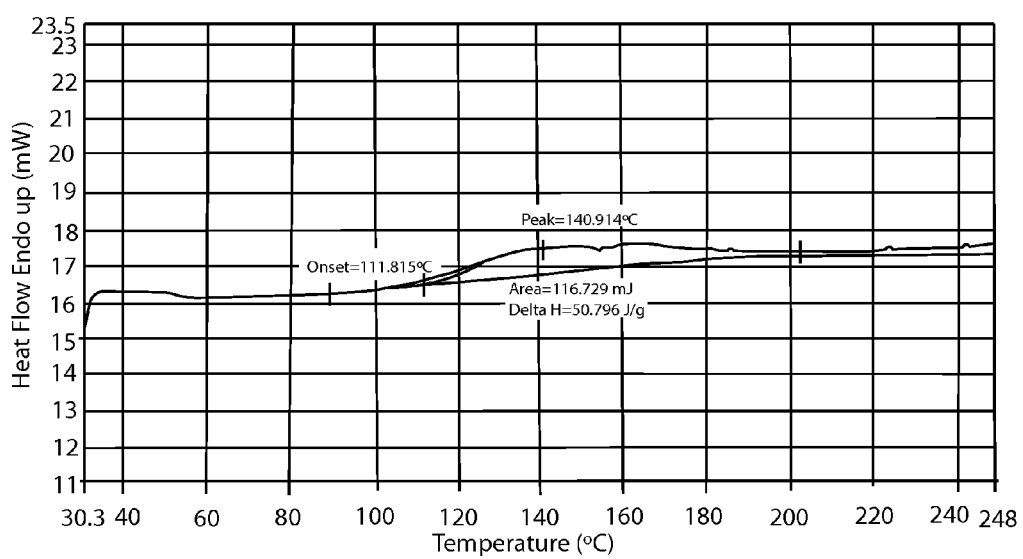
Figure 5:
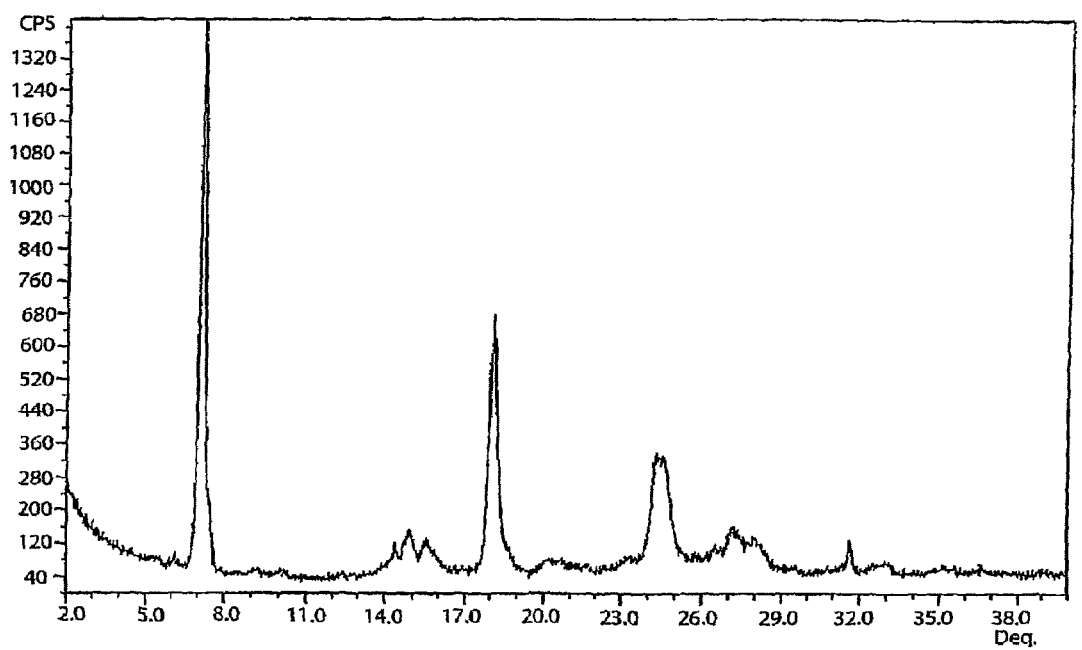

XRPD and DSC spectra for Form IV are shown in FIGS. 5 and 6, respectively.

Example 5

Preparation of a Mixture of Forms I and IV of 5-CNAC

A mixture of Forms I and IV of 5-CNAC was prepared as follows. A clean 200 gallon glass-lined reactor was charged with 525 of acetone. The reactor was purged with nitrogen. Agitation was started. To the stirring reactor contents were charged 35 kg of 5-CNAC. The reactor contents were heated to between 50 and 60° C. and held at this temperature for at least 20 minutes. During this time the majority of the solids dissolved. The reactor contents were pumped through a pressure filter into an adjacent 200 gallon glass-lined reactor. The initial reactor and pressure filter were rinsed into the second reactor with 20 L of fresh acetone. An aqueous sodium hydroxide solution was prepared in a separate tank by dissolving 8.92 kg of sodium hydroxide in 44.6 L of purified water. This aqueous base solution was pumped into the reactor containing the acetone/5-CNAC filtrate. This aqueous base addition caused the reactor contents to reflux. The aqueous base tank was rinsed with 8.9 L of fresh water into the refluxing reactor. No heat or cooling was applied to the reaction vessel and the reactor contents were allowed to slowly cool to ambient temperature. Cooling was applied to the reactor jacket and the reaction contents further cooled to between 0° C. and 5° C. This entire cooling cycle took between 16 and 24 hours. The precipitate that had formed in the reaction mixture was recovered by centrifuge filtration. The filter cake was placed in a drying oven and dried at 60° C. and full vacuum for at least 16 hours. The yield of dried disodium 5-CNAC monohydrate was about 39.9 kg. This 5-CNAC monohydrate was found to be a mixture of forms I and IV. The Form IV was found to convert to Form I over time on storage of the material.

All patents, applications, articles, publications, and test methods mentioned above are hereby incorporated by reference.

We claim:

1. A process for preparing a solid mixture of Forms I and IV of the disodium salt of N-(5-chlorosalicyloyl)-8-aminocaprylic acid comprising the step of cooling a solution of the disodium salt of N-(5-chlorosalicyloyl)-8-aminocaprylic acid and acetone for a sufficient time to precipitate the mixture of Forms I and IV, wherein the mixture exhibits an X-ray powder diffraction pattern having at least one peak in degrees 2Θ±0.2° 2Θ selected from 7.1, 10.4, 14.2, 15.0, 15.5, 16.1, 18.4, 20.9, 23.6, 24.1, 24.5, 24.9, 25.4, 26.6, 27.2, 27.5, 29.7 and 31.5 and at least one peak in degrees 2Θ±0.2° 2Θ selected from 7.1, 18.4 and 24.9.

2. The process of claim 1, wherein the mixture exhibits an X-ray powder diffraction pattern having at least two peaks in degrees 2Θ±0.2° 2Θ selected from 7.1, 10.4, 14.2, 15.0, 15.5, 16.1, 18.4, 20.9, 23.6, 24.1, 24.5, 24.9, 25.4, 26.6, 27.2, 27.5, 29.7 and 31.5.

3. The process of claim 1, wherein the mixture exhibits an X-ray powder diffraction pattern having at least one peak in degrees 2Θ±0.2° 2Θ selected from 15.5, 24.5 and 24.9.

4. The process of claim 1, wherein the mixture exhibits an X-ray powder diffraction pattern having peaks in degrees 2Θ±0.2° 2Θ at 7.1, 18.4 and 24.9.

* * * * *